US010231901B2

(12) United States Patent
Swartz

(10) Patent No.: US 10,231,901 B2
(45) Date of Patent: Mar. 19, 2019

(54) SEXUAL STIMULATION DEVICE

(71) Applicant: Megan Swartz, Las Vegas, NV (US)

(72) Inventor: Megan Swartz, Las Vegas, NV (US)

(73) Assignee: Megan Swartz, Las Vegas, NV (US)

( * ) Notice: Subject to any disclaimer, the term of this patent is extended or adjusted under 35 U.S.C. 154(b) by 133 days.

(21) Appl. No.: 15/598,153

(22) Filed: May 17, 2017

(65) Prior Publication Data

US 2017/0333282 A1 Nov. 23, 2017

Related U.S. Application Data

(60) Provisional application No. 62/337,798, filed on May 17, 2016.

(51) Int. Cl.

*A61F 5/00* (2006.01)
*A61H 19/00* (2006.01)
*A61H 23/02* (2006.01)

(52) U.S. Cl.

CPC ............ *A61H 19/44* (2013.01); *A61H 19/34* (2013.01); *A61H 23/02* (2013.01); *A61H 2201/1207* (2013.01); *A61H 2201/5071* (2013.01)

(58) Field of Classification Search

CPC ........ A61H 19/00; A61H 19/40; A61H 19/44; A61H 19/50; A61H 23/00

USPC ........................................ 600/38–41; 601/46

See application file for complete search history.

(56) References Cited

U.S. PATENT DOCUMENTS

2014/0350333 A1* 11/2014 Stout ...................... A61H 19/44 600/38
2017/0189264 A1* 7/2017 Ross ...................... A61H 19/44
2017/0224579 A1* 8/2017 Green .................... A61H 19/44
2018/0185237 A1* 7/2018 Baetica .................. G08C 17/02
2018/0325769 A1* 11/2018 Scheuring ............. A61B 7/023

* cited by examiner

*Primary Examiner* — John Lacyk
(74) *Attorney, Agent, or Firm* — Kunzler, PC

(57) ABSTRACT

A device for mutual sexual stimulation of partners is provided. The device includes a central area forming a base for at least three arms that extend therefrom in a common plane, the three arms comprising a pair of outer arms and an inner arm that is disposed in the common plane between the outer arms, where each of the outer arms includes at least one pressure sensor and at least one vibration motor. The device also includes a controller operatively coupled with the at least one pressure sensor and the at least one vibration motor, and configured to detect a pressure applied to a first outer arm of the pair of outer arms and activate the vibration motor in a second outer arm of the pair of outer arms in response to the detected pressure.

20 Claims, 12 Drawing Sheets

SEXUAL STIMULATION DEVICE

CROSS-REFERENCES TO RELATED APPLICATIONS

This application claims the benefit of U.S. Provisional Patent Application No. 62/337,798 entitled "SEXUAL STIMULATION DEVICE" and filed on May 17, 2016 for Megan Swartz, which is incorporated herein by reference.

FIELD

This application relates generally to sexual stimulation devices. In particular, this application relates to a sexual stimulation device that detects the sexual arousal of one partner and mimics that state of arousal to another partner.

BACKGROUND

Many sexual stimulation devices exist and are available for couples use. These devices typically are configured with a shape and or texture designed to stimulate sexual arousal. Some of these devices also include eccentric motors to create a vibrating simulation to the user. Heterosexual partners, whether using a sexual stimulation device or not, can typically detect when a partner is highly aroused because the Kegel muscles of the female partner will squeeze the penis of the male partner. Unfortunately, homosexual partners, and especially lesbian partners, do not have a way to have a similar experience, and no sexual stimulation device exists to replicate this experience.

SUMMARY

A device, system, and method for mutual sexual stimulation of partners is provided. The device enables partners, especially lesbian partners, to experience the level of sexual excitement their partner is experiencing through a feedback/response device. The device includes a central area forming a base for at least three arms that extend therefrom in a common plane, the three arms comprising a pair of outer arms and an inner arm that is disposed in the common plane between the outer arms, where each of the outer arms includes at least one pressure sensor and at least one vibration motor. The device also includes a controller operatively coupled with the at least one pressure sensor and the at least one vibration motor, and configured to detect a pressure applied to a first outer arm of the pair of outer arms and activate the vibration motor in a second outer arm of the pair of outer arms in response to the detected pressure.

In one embodiment, each of the pair of outer arms are telescopically coupled to the central area, or each of the pair of outer arms comprises accordion folds to allow each of the pair of outer arms to transition from an extended position to a retracted position. In another embodiment, the inner arm comprises a shape configured to engage an external surface of a user, and each of the pair of outer arms comprises a shape configured to insert into a user and engage an internal surface of the user.

In one embodiment, the controller is further configured to detect pressure applied to the second outer arm and activate the vibration motor in the first outer arm in response to the detected pressure. Alternatively, the controller is further configured to identify a pressure pattern applied to one of the first arm and activate the vibration motor in the second outer arm with a vibration pattern that substantially mimics the pressure pattern.

In one embodiment, the central area, the at least three arms, and the controller are encompassed by an outer covering that forms a substantially waterproof barrier. Furthermore, the at least one pressure sensor of each of the outer arms may be disposed between the outer covering and its respective outer arm. In one embodiment, the controller is configured to operate in at least one of a vibration only mode or a feedback/response mode. The device may include an input button for receiving user preferences from a user.

In one embodiment, the system includes a framework comprising a central area and three arms extending out from the central area in a common plane, where the three arms comprise a first outer arm, a second outer arm, and an inner arm disposed between the first outer arm and the second outer arm, where the framework includes a first set of accordion folds coupling the first outer arm to the central area and a second set of accordion folds coupling the second outer arm to the central area, and where the framework further comprises a plurality of pressure sensors and a plurality of vibration motors.

The system also includes a controller coupled to the framework, the controller comprising a processing device in communication with the plurality of pressure sensors and the plurality of vibration motors. The processing device is configured to detect a pressure pattern applied to first outer arm, and activate at least one of the plurality of vibration motors disposed on the second outer arm with a vibration pattern having an intensity and duration selected in response to the detected pressure pattern. The system may also include an outer covering encasing the framework.

The method includes, in one embodiment, providing the system as described above and detecting a pressure pattern applied to first outer arm, and activating at least one of the plurality of vibration motors disposed on the second outer arm with a vibration pattern having an intensity and duration selected in response to the detected pressure pattern.

BRIEF DESCRIPTION OF THE DRAWINGS

A more particular description of the embodiments briefly described above will be rendered by reference to specific embodiments that are illustrated in the appended drawings. Understanding that these drawings depict only some embodiments and are not therefore to be considered to be limiting of scope, the embodiments will be described and explained with additional specificity and detail through the use of the accompanying drawings, in which.

DETAILED DESCRIPTION

Figure 1:
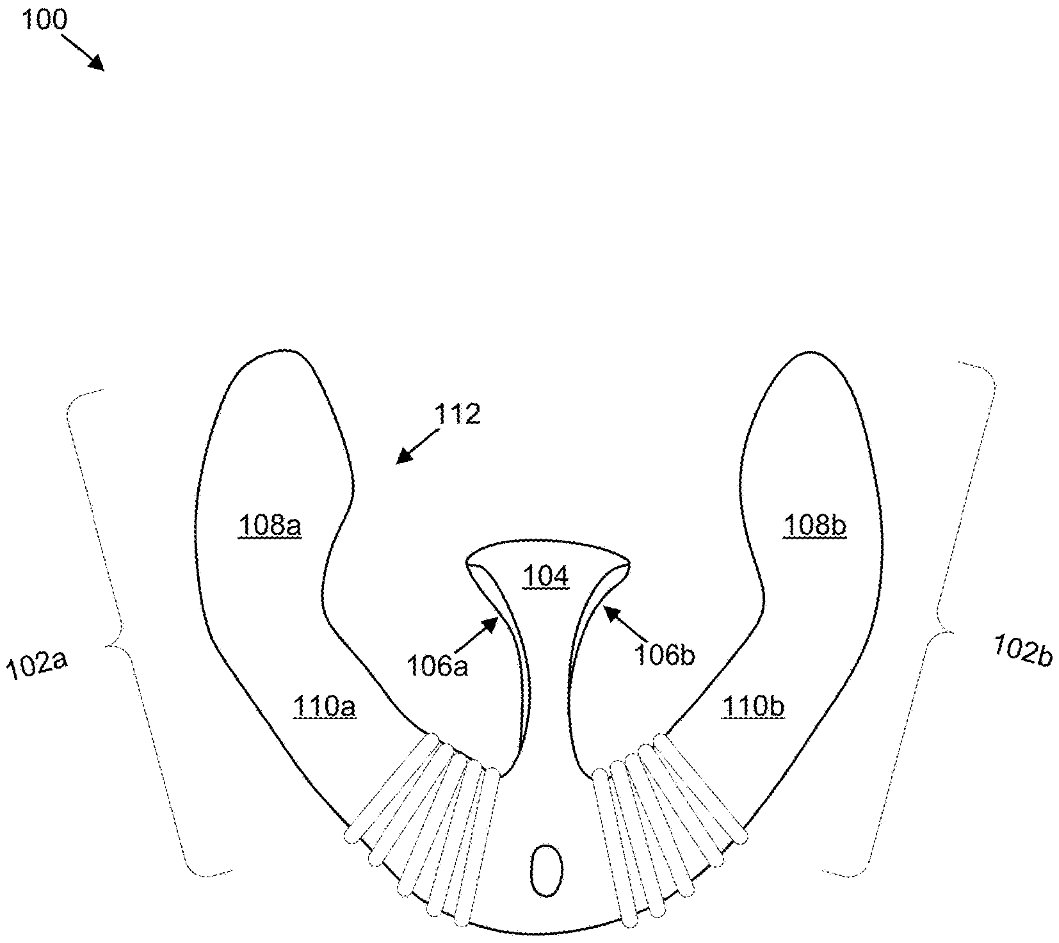
FIG. 1 is a side view diagram illustrating one embodiment of a sexual stimulation device in accordance with embodiments of the present invention.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory ("RAM"), a read-only memory ("ROM"), an erasable programmable read-only memory ("EPROM" or Flash memory), a static random access memory ("SRAM"), a portable compact disc read-only memory ("CD-ROM"), a digital versatile disk ("DVD"), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program instructions may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Furthermore, the described features, structures, or characteristics of the embodiments may be combined in any suitable manner. In the following description, numerous specific details are provided to give a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

The description of elements in each figure may refer to elements of proceeding figures. Like numbers refer to like elements in all figures, including alternate embodiments of like elements. Similar elements may be referred to with a number and a letter, such as "102*a*" and "102*b*", when identified individually, and when referred to jointly by the number only (i.e., "102" without that "a" or "b").

FIG. 1 is a side view diagram illustrating one embodiment of a sexual stimulation device 100 in accordance with embodiments of the present invention. The sexual stimulation device (hereinafter "device") 100, in one embodiment is formed having a general "W" shape that is configured to provide a feedback response between two sexual partners. It is contemplated, however, that the concepts and components described herein below may be adapted to a device that accommodates three or more sexual partners. The device 100 includes a pair of outer arms 102*a*, 102*b* and an inner arm 104. Each of the outer arms 102*a*, 102*b* are configured and dimensioned with an anatomical shape for engaging an internal surface of the sexual partners. Stated differently, each of the outer arms 102, for example, may be inserted into the vagina or anus of one of the sexual partners. The inner arm 104, conversely, is configured with surfaces 106*a*, 106*b* for engaging external surfaces of the sexual partners (i.e., the clitoris).

In the depicted embodiment, opposing sides of the inner arm 104 are configured with a curved profile for engaging the clitoral area of the sexual partners. As such, the depicted device 100 is configured to simultaneously stimulate the vagina and clitoris of both sexual partners. When both partners face each other, the outer arm 102*a* and surface 106*a* act to stimulate the first partner while the second outer arm 102*b* and surface 106*b* stimulate the second partner.

Although not depicted here, the inner arm 104 may be replaced with an inner arm that is configured with a surface 106*a* for stimulating a clitoral area and a surface (e.g., a ring) for stimulating a penis. It is also anticipated that the inner arm 104 may be replaced with an inner arm that is adapted for stimulating two male partners instead of the depicted embodiment for two female partners. For example, the inner arm 104 may be replaced with a shaft that extends between the outer arms 102*a*, 102*b*, and includes a pair of rings, where each ring is adapted for engaging one penis. In an alternative embodiment, the inner arm 104 may be replaced with other surfaces and/or shapes that differently engage the clitoral area. One example of a different surface is depicted below with reference to FIGS. 7-12.

Each of the outer arms 102 may be formed with a bulbous head 108, as depicted that narrows to an extendible arm 110. The bulbous head 108, as described above, is configured for insertion into one of the sexual partners. The bulbous head 108, in one embodiment, has a side profile (as depicted) that is configured to lie against the region of the vagina near where the G-spot is located, as indicated by arrow 112.

The device 100, in one embodiment, is formed with an inner frame (not depicted) and an outer covering. The outer covering, in one embodiment, is formed of medical grade silicone, vinyl, rubber or other suitable material. The inner frame may be formed of a rigid polymer or composite material. The inner frame is configured to adapt to the vigorous movements of the sexual partners. In other words, the inner frame is adapted to allow the outer arms 108*a* to move towards and away from each other and withstand the movement of the partners with reference to each other. Additionally, the inner frame is configured to bias the outer arms 108*a* 108*b* towards each other and thereby apply a constant pressure on the G-spot to aid in stimulation of the sexual partners.

Figure 2:
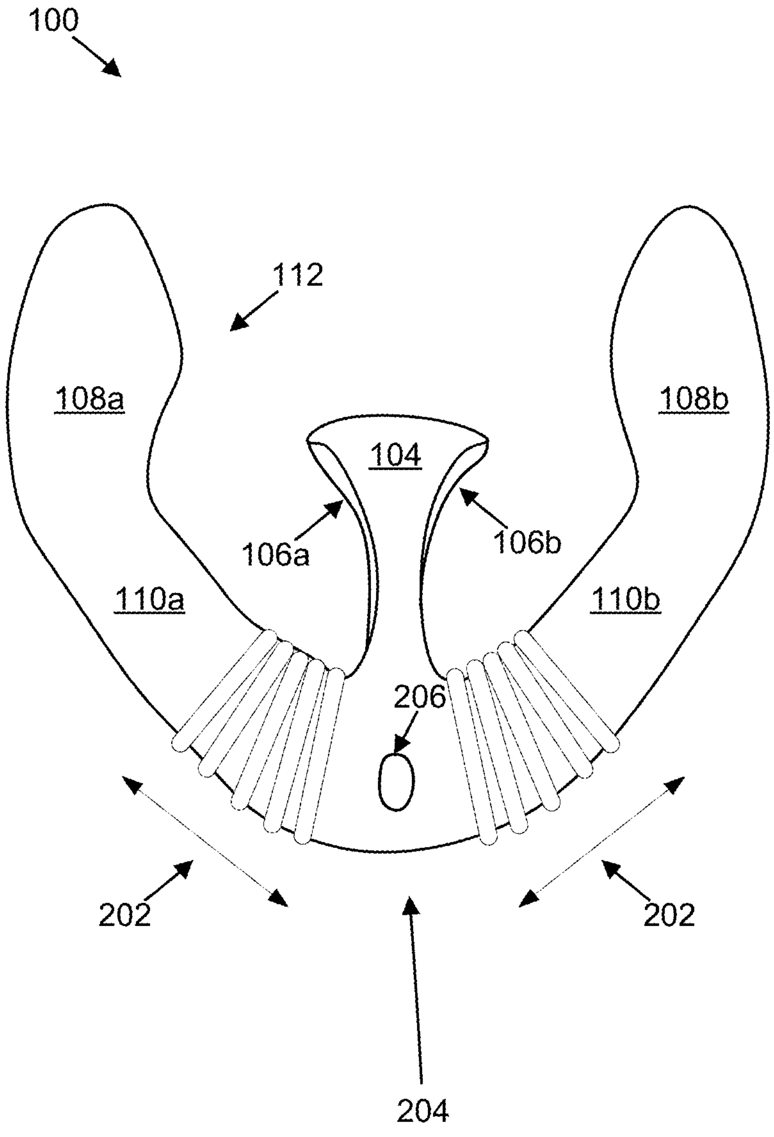
FIG. 2 is another side view diagram illustrating the device in accordance with embodiments of the present invention.

FIG. 2 is another side view diagram illustrating the device 100 in accordance with embodiments of the present invention. In the depicted embodiment, the outer arms 102 are configured to telescope into and out of a center area 204, as depicted by arrows 202. The outer arms 102 may be formed with, as depicted, an accordion style (e.g., accordion folds) inner frame that is covered by the medical grade silicone having a series of bulges to allow for the extension of the accordion folds. Other styles of extendable arms are contemplated. The extendable arms 102 allow the device to be sized for use with larger and/or smaller sexual partners by allowing the arms to transition from an extended position to a retracted position. Extending one or both arms 102 outward allows for the device 100 to be used by sexual partners with larger than average, for example, abdomens.

In one embodiment, the device 100 includes one or more buttons 206 for receiving input from the sexual partners. The button 206 is configured to receive the input and communicate the input with a controller, as will be described below in greater detail. The button 206 is configured to detect any number of input presses to activate any number of operating modes, including but not limited to, a standard hi, medium, and low operating mode, and a feedback/response mode (i.e., "Show me yours" mode). Additionally, the button may activate any number of vibration wave patterns.

Figure 3:
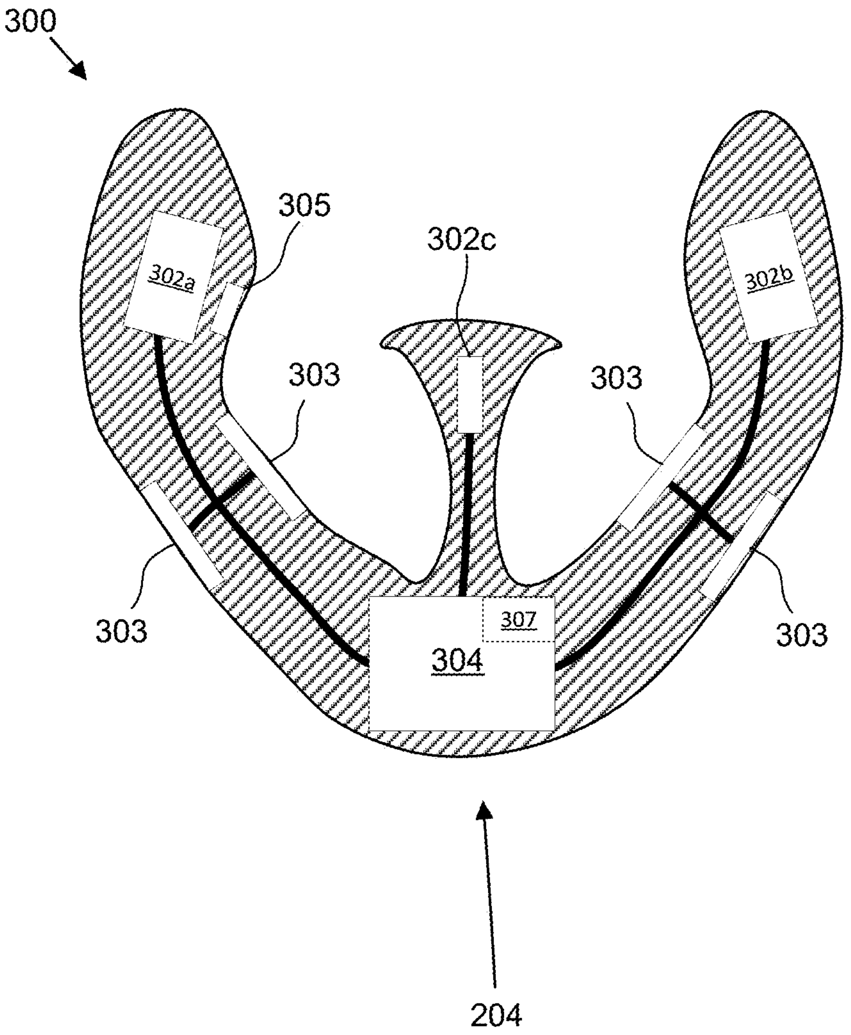
FIG. 3 is a schematic block diagram illustrating a cross-sectional view of one embodiment of the device in accordance with embodiments of the present invention.

FIG. 3 is a schematic block diagram illustrating a cross-sectional view of one embodiment of the device 100 in accordance with embodiments of the present invention. The device 100, in one embodiment, is formed with one or more vibration motors 302. Each of the vibration motors 302 are configured to provide a vibrating stimulus to an area of the sexual partner that is adjacent the vibration motor 302. Each of the vibration motors 302 may be provided with a rotating eccentric weight (not shown) for generating the vibration stimulus. One or more motors may be positioned in each of the arms that extends outward from the central area 204. Stated differently, each outer arm 102 may have one or more vibration motors 302*a*, 302*b*. The inner arm 104 may also include a vibration motor 302*c* that is configured for providing vibration stimulus.

The device 100, in one embodiment also includes a plurality of pressure sensors 303. The pressure sensors 303 may be disposed between the outer covering and the inner frame to detect when pressure is being applied to one or more of the arms (i.e., when pressure is detected on one of the outer arms). The pressure sensor 303 may include a pressure or other strain or force sensor, such as a load cell, strain gauge or other sensor capable of monitoring a degree of force applied to an area of the arm adjacent the pressure sensor 303. The pressure sensors 303 may be positioned radially around a circumference of the arm just below the bulbous head. Alternatively, pressure sensors 303 may be positioned around the exterior surface of the bulbous head, and in another embodiment in both of the above-described locations. The pressure sensors 303, in one embodiment, detect when one of the sexual partners is reaching an excited state as indicated by a contraction of Kegel muscles. In further embodiments, pressure sensors 303 may also be positioned in any location of the device.

In yet another embodiment, the pressure sensor 303 may include a temperature sensor. The temperature sensor may be useful for determining when one or more of the arms 104, 108 is in contact with a person. This information may be utilized to enable or disable, for example, sensors, motors, etc.

Each of the vibration motors 302, pressure sensors 303, and warming devices 305 are in electrical communication with the controller 304. The feedback from the pressure sensors 303 is provided to the controller 304, which, as will be described in greater detail below, is configured to modify the output of the vibration motors 302 in response to the pressure sensor 303 feedback. A battery is operatively coupled with the controller 304, which controls the output of the vibration motors 302 by modulating the power and/or signal sent to the vibration motors 302 from the battery. In one embodiment, the battery is a rechargeable battery 307 disposed within the central area 204. The device 100 may have a port for connecting with an external power source to recharge the battery 307. In another embodiment, the device 100 is adapted for inductive charging (i.e., wireless charging) of the battery. As such, the device 100 contains no openings and is therefore substantially waterproof In another embodiment, the device 100 may be configured with heating elements 305. The heating elements may be integrated with the pressure sensors, or alternatively positioned separately from the pressure sensors 303. The heating elements 305 may also be electrically coupled with the controller 304 and controllable by the controller 304. Other sensors are contemplated, including but not limited to, a moisture sensor, a temperature sensor, etc. In other words, any sensor that may be useful for indicating an elevated state of arousal may be implemented into the device 100 and used by the controller 304 to modulate the vibration patterns of the vibration motors (or other stimulus inducing components such as the heating elements) to increase the state of arousal of the other sexual partner.

As will be discussed in greater detail below, a compression of the pressure sensors 303 by, for example, Kegel muscles on a first outer arm may be mirrored to the second outer arm by modulating the vibration motor 302*b* in a way that mirrors a squeezing pattern of the first sexual partner on the first outer arm. In other words, when the first sexual partner is excited and squeezing the first outer arm inside of her vagina, this squeezing can be mirrored to the second sexual partner by modulating (i.e., increasing and decreasing) the vibration pattern of the second vibration motor 302*b* in the vagina of the second sexual partner. Beneficially, this allows the second sexual partner to experience the state of arousal of the first sexual partner, which was previously impossible in lesbian sexual partners.

Figure 4:
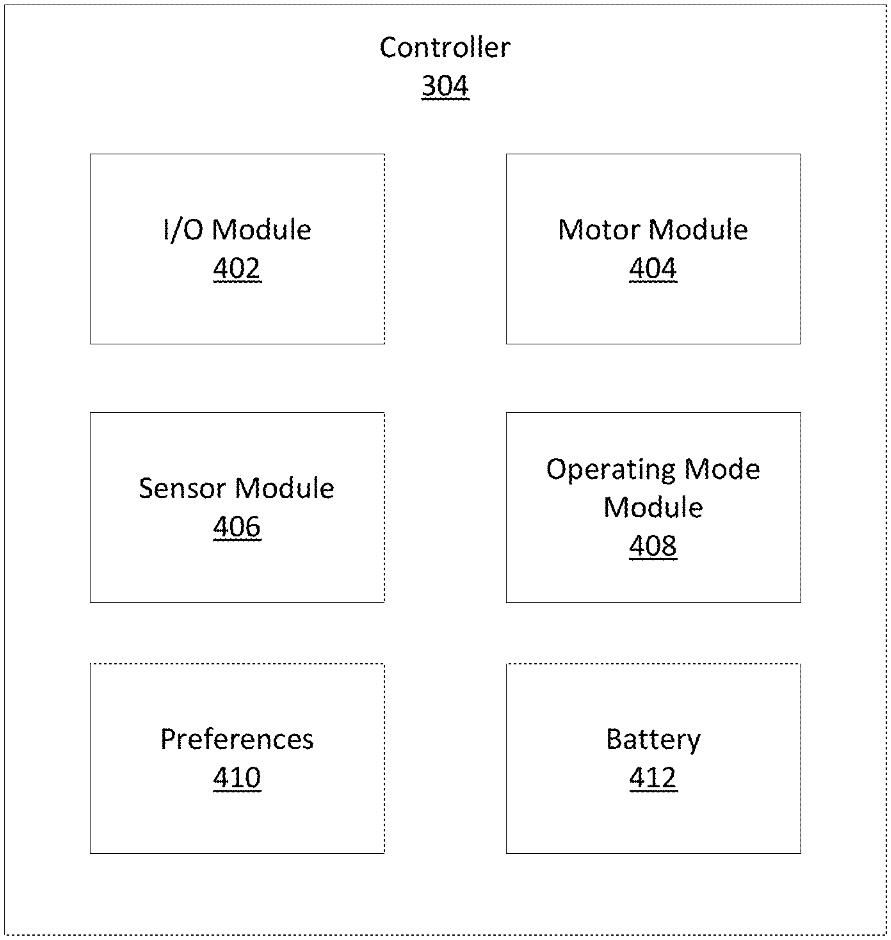
FIG. 4 is a schematic block diagram illustrating one embodiment of the controller in accordance with embodiments of the present invention.

FIG. 4 is a schematic block diagram illustrating one embodiment of the controller 304 in accordance with embodiments of the present invention. In one embodiment, the controller 304 is a hardware circuit comprising custom circuits or gate arrays, off-the-shelf semiconductors such as logic chips, transistors, or other discrete components that implement a processor. The controller 304 may also be implemented as a module that is described above.

In one embodiment, the controller 304 includes an input/output (I/O) module 402, a motor module 404, a sensor module 406, an operating mode module 408, preferences 410, and a battery 412. The I/O module 402, in one embodiment, is configured to receive input from external sources. For example, the I/O module 402 may communicate with the button 206 to receive input from a user. A user may depress the button, and the I/O module 402 is configured to identify the user action and communicate the user action with the controller 304. The I/O module 402 may also include one or more radios that enable wireless communication with a remote controller. The remote controller may be, in one embodiment, a device with buttons to toggle between different operating modes. In an alternative embodiment, the I/O module 402 may be configured to communicate with a handheld electronic device such as a smart phone. The smart phone may communicate with the I/O module 402 over any suitable communication protocol including, but not limited to, Bluetooth® and/or Wi-Fi®. As such the I/O module 402 may receive input from a user via a touchscreen interface that allows a user to design, for example, custom vibration wave patterns, custom vibration motor response levels (e.g., amplify the standard vibration level), etc.

The motor module 404, in one embodiment, is configured to modulate the power applied to one or more of the vibration motors. The motor module 404 is configured to receive input from the sensor module 406 and accordingly modify the output of one or more vibration motors in response to the input. Alternatively, the motor module 404 may be configured to cycle the vibration motors through various predetermined or predefined vibration wave patterns. In another embodiment, the motor module 404 is configured to maintain a steady vibration pattern in the one or more vibration motors.

The sensor module 406 is configured to communicate with the one or more pressure sensors 406. The sensor module 406 receives input from the pressure sensors that indicate an increase in pressure on the outer arms (i.e., elevated arousal due to squeezing of the outer arm by the Kegel muscles) or the inner arm (i.e., elevated arousal due to increased pushing of one sexual partner on the other partner). The sensor module 406, as described above, may also be configured to communicate with any sensor that may be indicative of increased arousal. Examples include, but are not limited to, motion sensors, moisture sensors, temperature sensors, etc. Any of these sensors may be used separately, or in combination with each other, to detect the state of arousal of one or more sexual partners.

The operating mode module 408, in one embodiment, is configured with various operating modes, including but not limited to, a standard operating mode and a response/feedback mode. In one embodiment, the standard operating mode activates the one or more vibration motors in one of the various vibration wave patterns. For example, the default standard operating mode may be an always on vibration (i.e., no pulsing) with a low, medium, or high intensity rating. Other operating modes may include a pulsing square wave (i.e., on, off, on, off, etc.), or any other of the contemplated wave patterns.

In another embodiment, the operating mode module 408 is configured to operate in a feedback/response mode. The feedback/response mode is a mode where the feedback of one sexual partner is converted into a response that is relayed to the other sexual partner via the vibration motor, or any other type of stimulus. For example, the feedback/response mode may be configured to activate the vibration motor of the second partner to mirror the input of the pressure sensors of the first partner. Stated differently, if the first partner is experiencing elevated states of sexual arousal and squeezing the first outer arm with Kegel muscles, the squeezing or pressure pattern (i.e., on-off, or alternatively, a constant squeeze) may be converted to an electrical signal or vibration pattern that simulates or substantially mimic the squeezing pattern (i.e., motor on-off, or alternatively, a constant motor vibration, with an intensity that approximates the squeezing pressure). The electrical signal may be modulated by the controller to approximate and simulate the input of the first partner to the second partner. Beneficially, this allows the second sexual partner to experience the arousal of the first partner much in a way that a heterosexual couple does when the Kegel muscles of a woman squeezes the penis.

In another embodiment, the operating mode module 408 may receive updates via the handheld electronic device (i.e., smart phone). If new operating modes are designed, these operating modes may be distributed to the device 100 via a download over a global communications network from a server. The download may include instructions that instruct the controller 304 to operate in a new operating mode, or to implement a new vibration pattern.

In one embodiment, the controller 304 includes user preferences 410. These user preferences may be programmed via a series of button input, or alternatively received via a remote control or other handheld electronic device. Examples of preferences 410 that may be stored in the controller include desired default operating mode (i.e., standard or feedback/response), default vibration intensities, default vibration patterns, alternative vibration patterns, etc. It is also contemplated that the preferences 410 may include instructions that cause the controller 304 to detect a certain feedback pattern (i.e., a specific squeezing pattern by the first partner) to trigger a different operating mode, a different vibration pattern, or a different vibration intensity. These principles may also be applied to different types of stimulus, including but not limited to, heating elements to warm an area adjacent the heating element.

Figure 5:
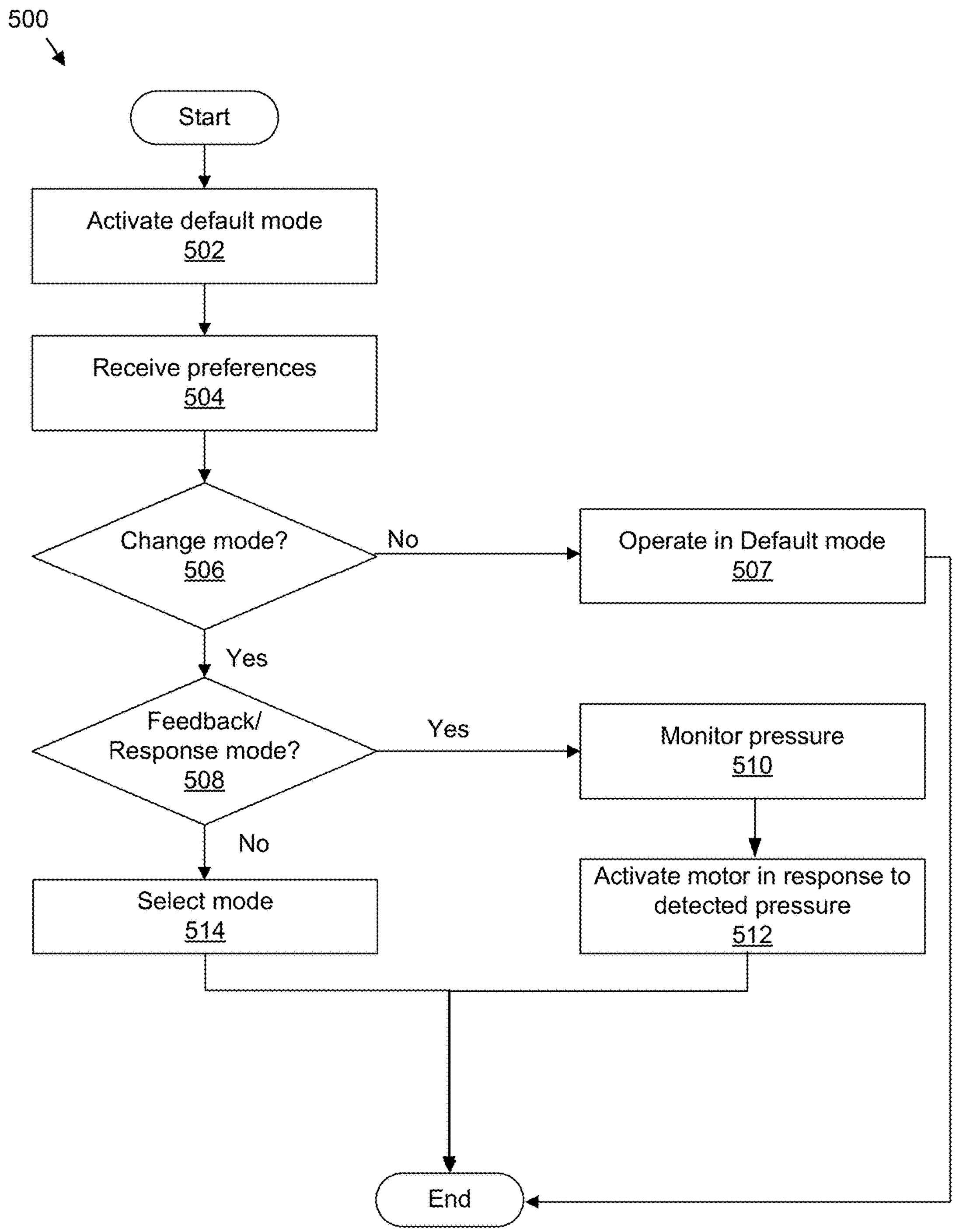
FIG. 5 is a schematic flow chart diagram illustrating one embodiment of a method for conveying the arousal state of one sexual partner to another partner in accordance with embodiments of the present disclosure.

FIG. 5 is a schematic flow chart diagram illustrating one embodiment of a method 500 for conveying the arousal state of one sexual partner to another partner in accordance with embodiments of the present disclosure. The method 500 starts and the controller activates 502 a default operating mode. For example, the controller may detect that a user has turned on the device 100 and the controller activates the vibration motors in a standard, low intensity mode. Alternatively, the controller detects that the user has previously identified a different default operating mode, and the controller activates that different operating mode as the default operating mode.

In some embodiments, the controller then receives 504 preferences from the user. These preferences may be received via the input button, or alternatively via a remote control or wirelessly from a smart phone. The controller then detects 506 if the user desires to change the operating mode. If the mode is not changed, the device continues to operate in the default operating mode, and the method ends. Alternatively, the device continues to operate 507 in the default operating mode until a mode change request is received.

If the controller detects a change mode request at block 506, then the controller determines if the requested mode is a different standard mode or if the requested mode is the feedback/response mode at block 508. If the feedback/response mode is selected, then the controller monitors the sensors at block 510. In one embodiment, the controller monitors the pressure sensors, or any other sensor that may be useful to indicate the arousal state of the sexual partners. In response to an increase in, for example, pressure on one or both of the outer arms, the controller activates a stimulus, at block 512, in response to the detected increase in pressure. For example, the controller may cause the motor to emulate the increase in pressure by increasing the vibration intensity of the other partner's vibration motor. This feedback and response loop may be operating simultaneously on both partners. In other words, the controller is capable of detecting the pressure of both arms simultaneously and separately modulating the vibration motors in response to the detected pressures. Additionally, the vibration motor of the inner arm may also be modulated in a similar manner.

If, at block 508, the feedback/response mode is not selected, the controller receives input indicating another operating mode and operates according to the selected mode. At this point, the method 500 ends.

Figure 6:
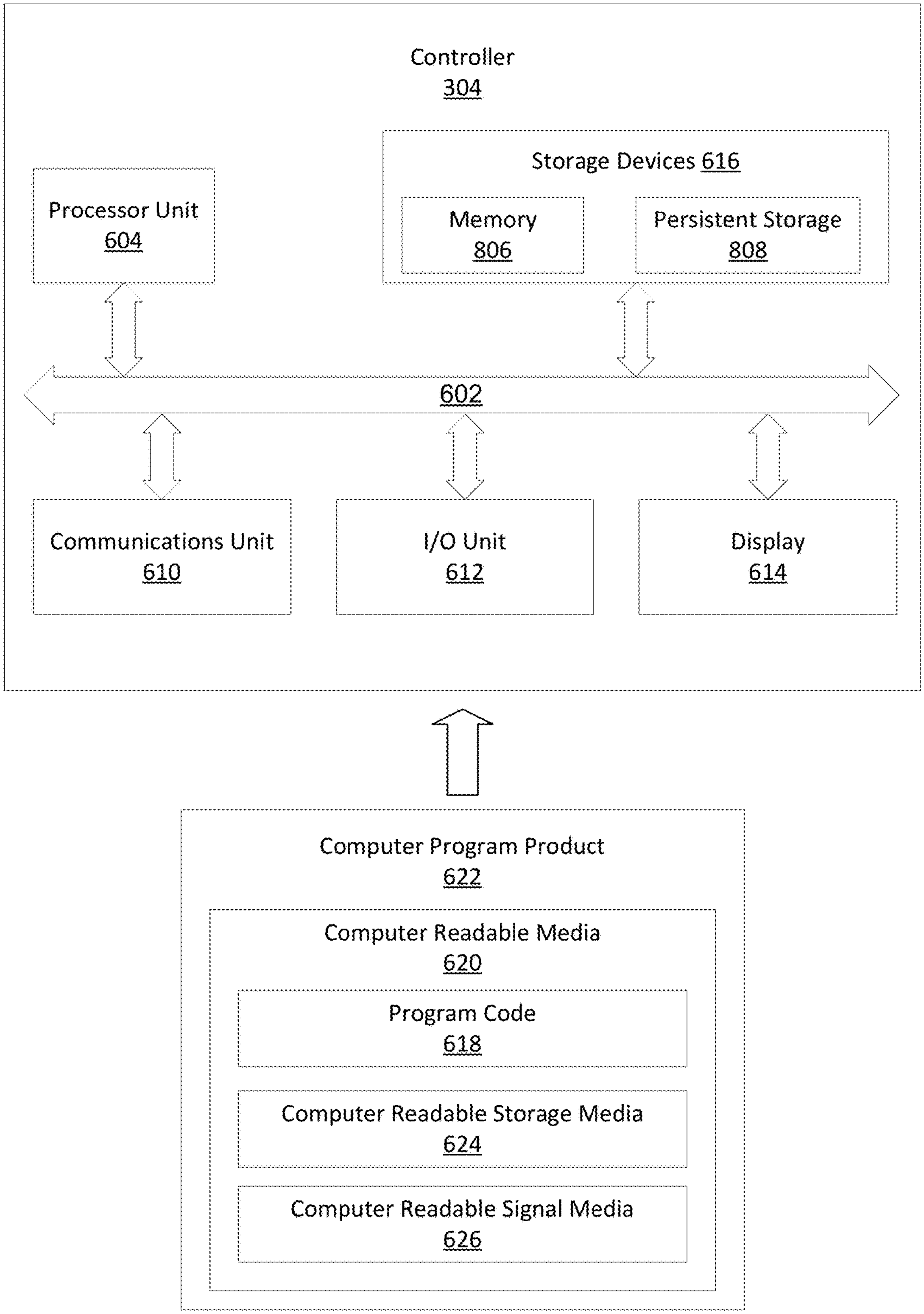
FIG. 6 is a schematic block diagram illustrating one embodiment of a controller in accordance with embodiments of the present disclosure.
Figure 7:
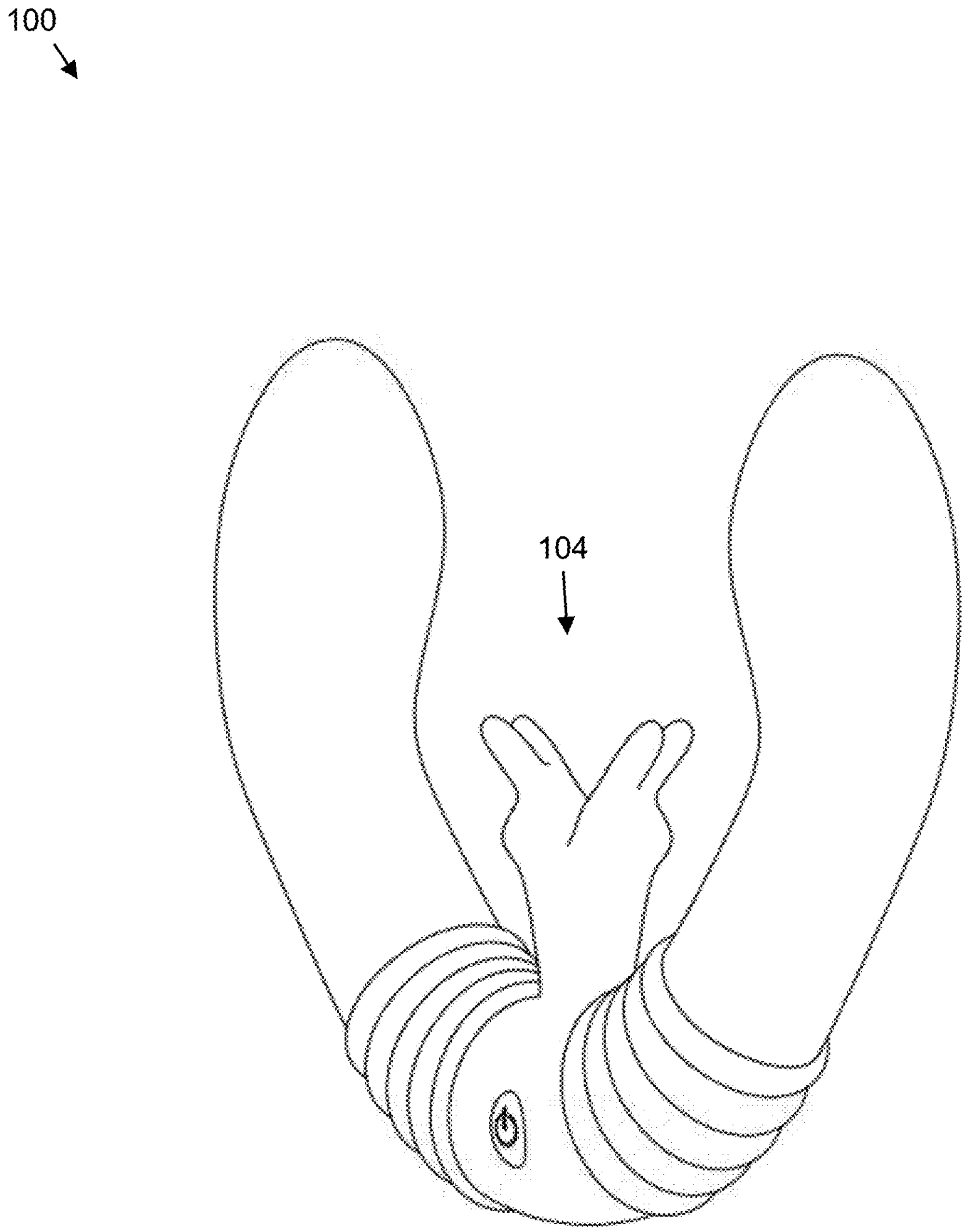
FIGS. 7-12 are perspective, front, back, top, bottom, and side view diagrams, respectively, of the device in accordance with embodiments of the present invention.
Figure 8:
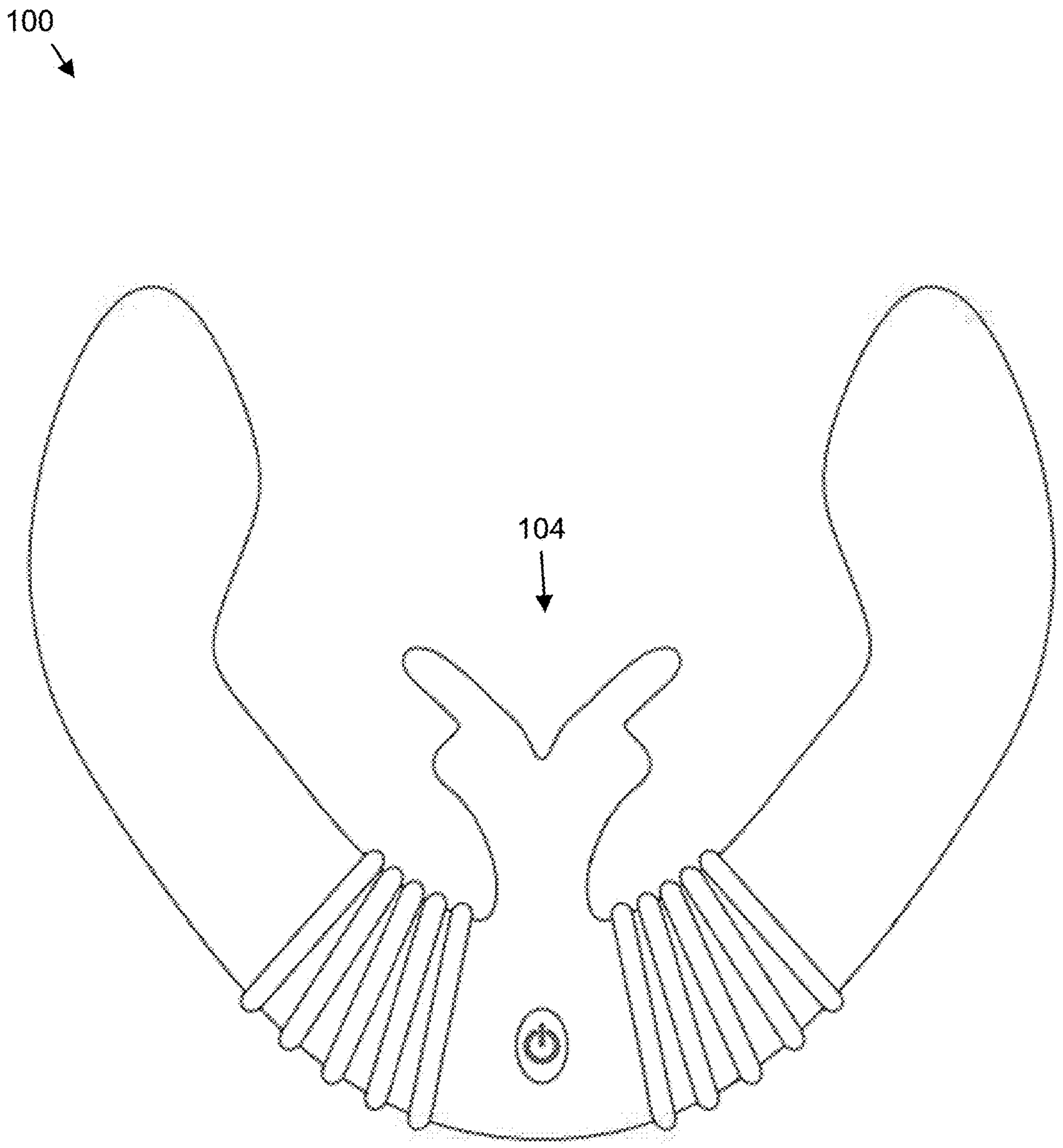
Figure 9:
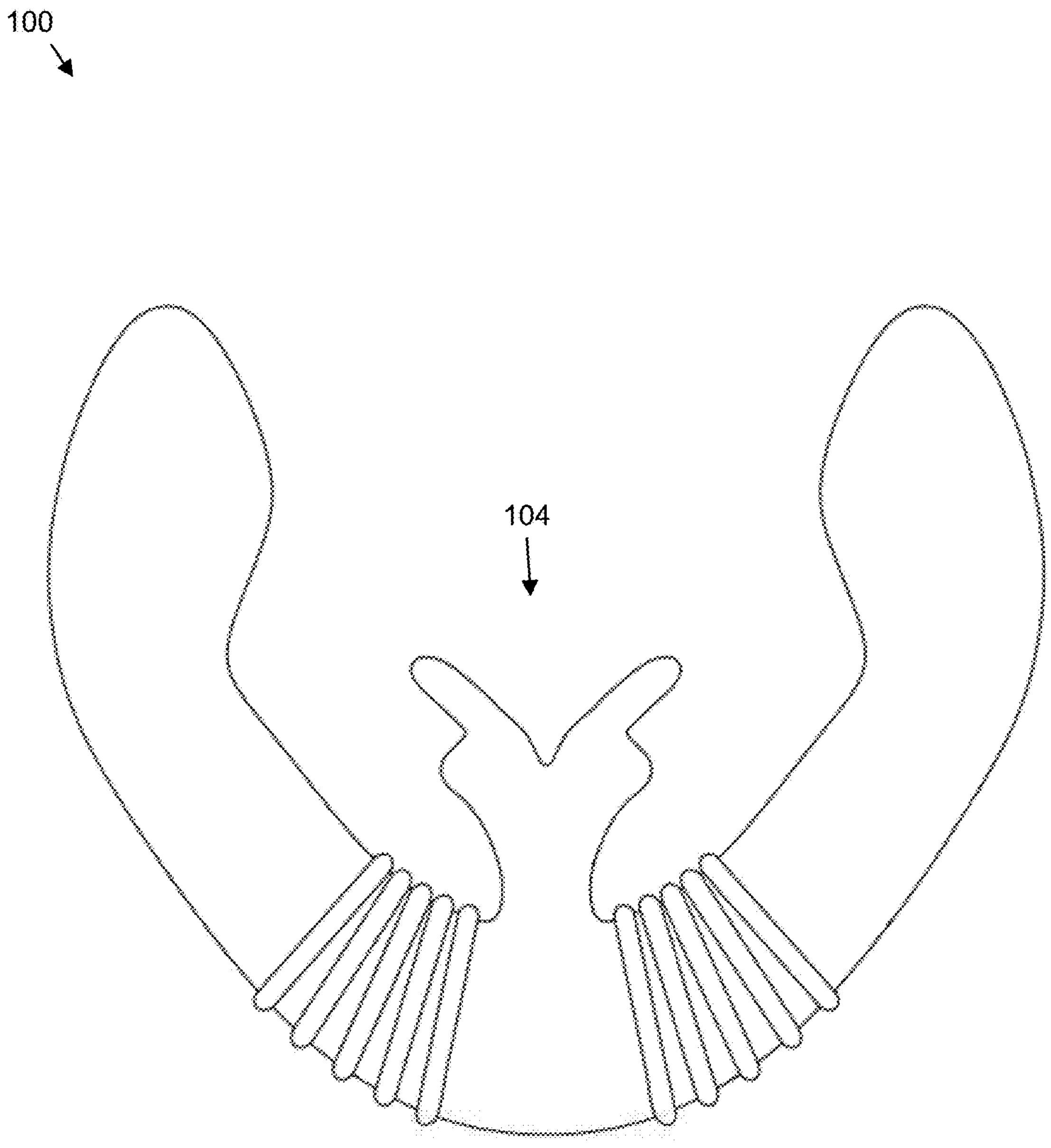
Figure 10:
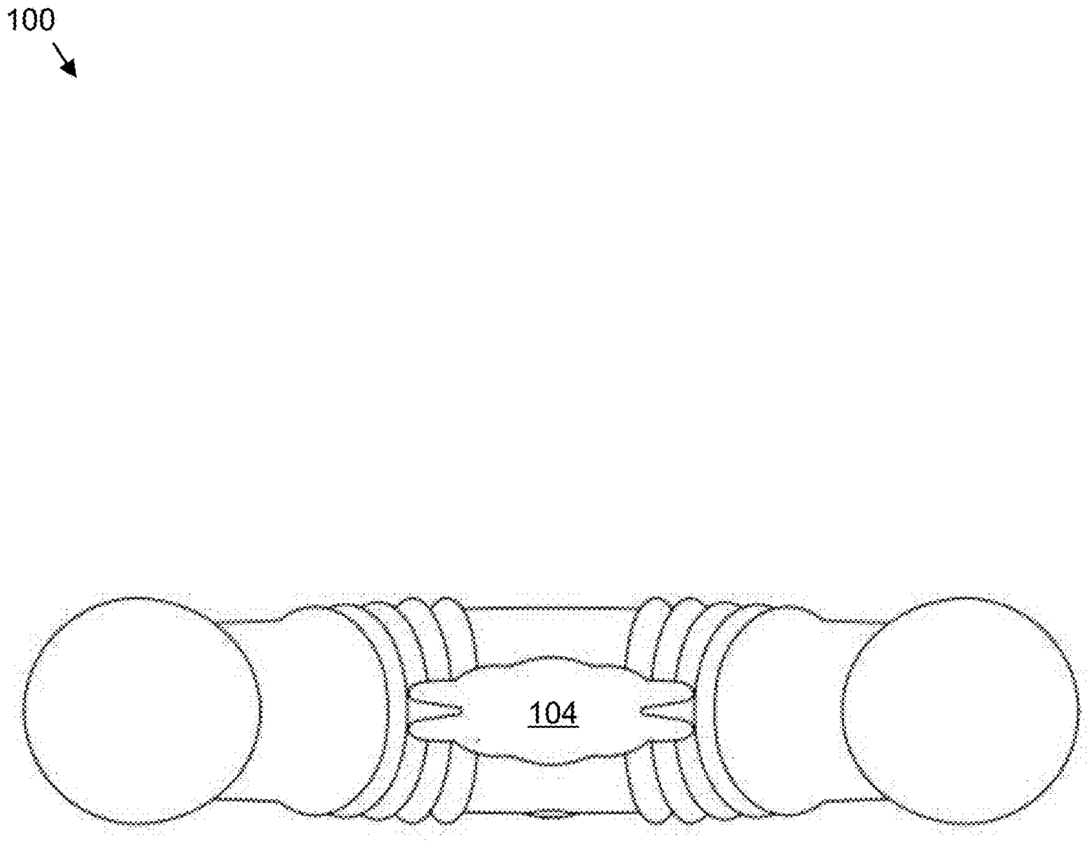
Figure 11:
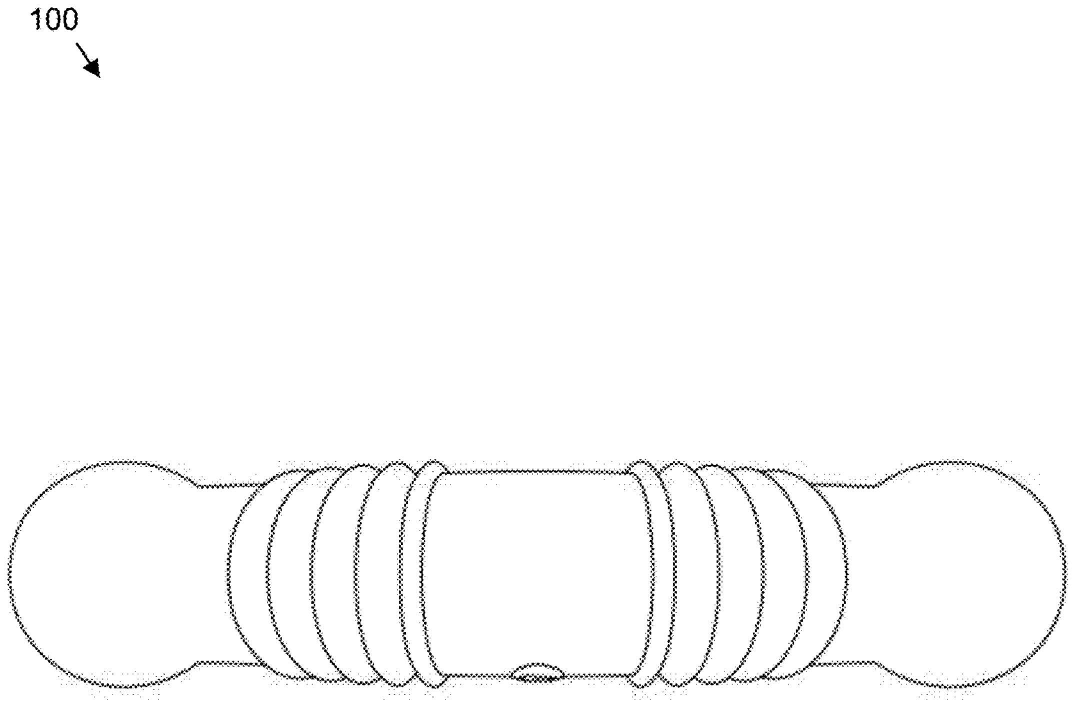
Figure 12:
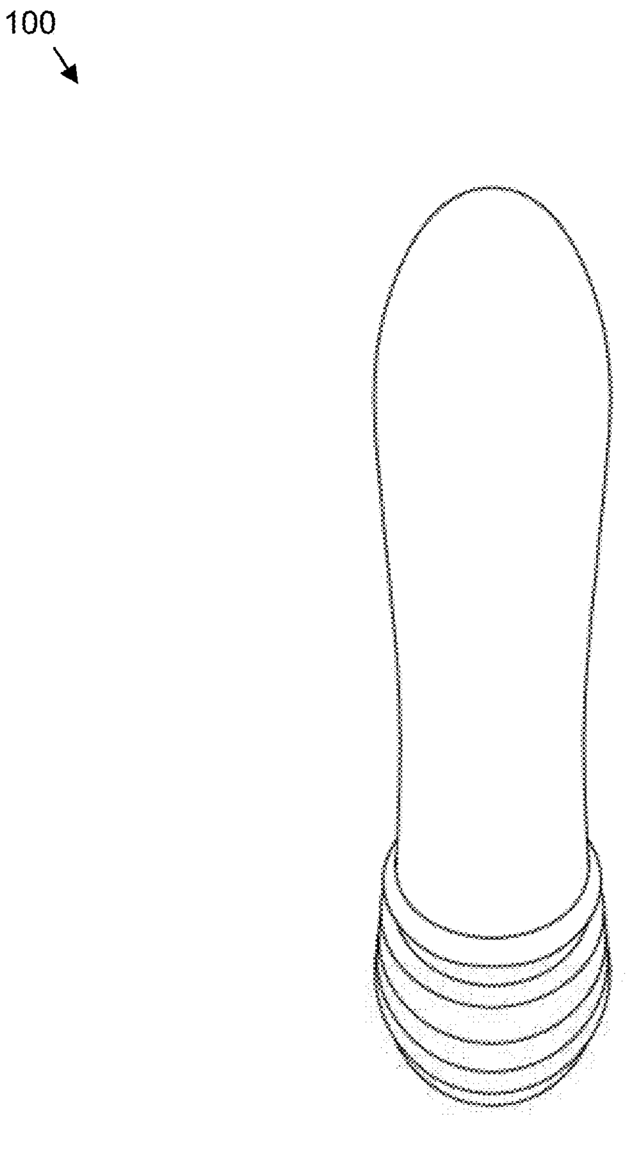

FIG. 6 is a schematic block diagram illustrating one embodiment of a controller 304 in accordance with embodiments of the present disclosure. The controller 304 is an example of a computing device, which may be used to implement one or more components of embodiments of the invention, and in which computer usable program code or instructions implementing the processes may be located for the illustrative embodiments. In this illustrative example, the information handling system includes communications fabric 602, which provides communications between a processor unit 604, memory 606, persistent storage 608, communications unit 610, input/output (I/O) unit 612, and display 614.

The processor unit 604 serves to execute instructions for software that may be loaded into memory 606. The processor unit 604 may be a set of one or more processors or may be a multi-processor core, depending on the particular implementation. Further, the processor unit 604 may be implemented using one or more heterogeneous processor systems, in which a main processor is present with secondary processors on a single chip. As another illustrative example, the processor unit 604 may be a symmetric multi-processor system containing multiple processors of the same type.

Memory 606 and persistent storage 608 are examples of storage devices 616. A storage device is any piece of hardware that is capable of storing information, such as, for example, without limitation, data, program code in functional form, and/or other suitable information either on a temporary basis and/or a permanent basis. Memory 606, in these examples, may be, for example, a random access memory, or any other suitable volatile or non-volatile storage device. Persistent storage 608 may take various forms, depending on the particular implementation. For example, persistent storage 608 may contain one or more components or devices. For example, persistent storage 608 may be a hard drive, a flash memory, a rewritable optical disk, a rewritable magnetic tape, or some combination of the above. The media used by persistent storage 608 may be removable. For example, a removable hard drive may be used for persistent storage 608.

The communications unit 610, in these examples, provides for communication with other data processing systems or devices. In these examples, the communications unit 610 is a network interface card. The communications unit 610 may provide communications through the use of either, or both, physical and wireless communications links.

The input/output unit 612 allows for the input and output of data with other devices that may be connected to data processing system 304. For example, the input/output unit 612 may provide a connection for user input through a keyboard, a mouse, and/or some other suitable input device. Further, the input/output unit 612 may send output to a printer. The display 614 provides a mechanism to display information to a user.

Instructions for the operating system, applications, and/or programs may be located in the storage devices 616, which are in communication with the processor unit 604 through the communications fabric 602. In these illustrative examples, the instructions are in a functional form on persistent storage 608. These instructions may be loaded into memory 606 for execution by the processor unit 604. The processes of the different embodiments may be performed by the processor unit 604 using computer implemented instructions, which may be located in a memory, such as the memory 606.

These instructions are referred to as program code, computer usable program code, or computer readable program code that may be read and executed by a processor in the processor unit 604. The program code, in the different embodiments, may be embodied on different physical or computer readable storage media, such as the memory 606 or the persistent storage 608.

Program code 618 is located in a functional form on computer readable media 620 that is selectively removable and may be loaded onto or transferred to the controller 304 for execution by the processor unit 604. The program code 618 and computer readable media 620 form computer program product 622. In one example, the computer readable media 620 may be a computer readable storage media 624 or a computer readable signal media 626. The computer readable storage media 624 may include, for example, an optical or magnetic disc that is inserted or placed into a drive or other device that is part of the persistent storage 608 for transfer onto a storage device, such as a hard drive, that is part of the persistent storage 608. The computer readable storage media 624 also may take the form of a persistent storage, such as a hard drive, a thumb drive, or a flash memory that is connected to controller 304. In some instances, the computer readable storage media 624 may not be removable from the controller 304.

Alternatively, the program code 618 may be transferred to the controller 304 using computer readable signal media 626. Computer readable signal media 626 may be, for example, a propagated data signal containing program code 618. For example, the computer readable signal media 626 may be an electromagnetic signal, an optical signal, and/or any other suitable type of signal. These signals may be transmitted over communications links, such as wireless communication links, an optical fiber cable, a coaxial cable, a wire, and/or any other suitable type of communications link. In other words, the communications link and/or the connection may be physical or wireless in the illustrative examples. The computer readable media also may take the form of non-tangible media, such as communications links or wireless transmissions containing the program code.

In some illustrative embodiments, the program code 618 may be downloaded over a network to the persistent storage 608 from another device or data processing system through the computer readable signal media 626 for use within the controller 304. For instance, program code stored in a computer readable storage media in a server data processing system may be downloaded over a network from the server to the controller 304. The system providing the program code 618 may be a server computer, a client computer, or some other device capable of storing and transmitting program code 618.

The different components illustrated for the controller 304 are not meant to provide physical or architectural limitations to the manner in which different embodiments may be implemented. The different illustrative embodiments may be implemented in a controller including components in addition to and/or in place of those illustrated for the controller 304. Other components shown in FIG. 8 can be varied from the illustrative examples shown. The different embodiments may be implemented using any hardware device or system capable of executing program code. For example, a storage device in the controller 304 is any hardware apparatus that may store data. The memory 606, persistent storage 608, and the computer readable media 620 are examples of storage devices in a tangible form.

In another example, a bus system may be used to implement communications fabric 602 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, the memory 606 or a cache such as found in an interface and memory controller hub that may be present in the communications fabric 602.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

FIGS. 7-12 are perspective, front, back, top, bottom, and side view diagrams, respectively, of the device 100 in accordance with embodiments of the present invention. In particular, FIGS. 7-10 depict, as described above, an alternative inner arm configured for stimulation of external surfaces of a user (i.e., the clitoris).

The embodiments may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A stimulating device comprising:

a central area forming a base for at least three arms that extend therefrom in a common plane, the three arms comprising a pair of outer arms and an inner arm that is disposed in the common plane between the outer arms, where each of the outer arms includes at least one pressure sensor and at least one vibration motor; and a controller operatively coupled with the at least one pressure sensor and the at least one vibration motor, and configured to detect a pressure applied to a first outer arm of the pair of outer arms and activate the vibration motor in a second outer arm of the pair of outer arms in response to the detected pressure.

2. The stimulating device of claim 1, where each of the pair of outer arms are telescopically coupled to the central area.

3. The stimulating device of claim 2, where each of the pair of outer arms comprises accordion folds to allow each of the pair of outer arms to transition from an extended position to a retracted position.

4. The stimulating device of claim 1, where the inner arm comprises a shape configured to engage an external surface of a user.

5. The stimulating device of claim 1, where each of the pair of outer arms comprises a shape configured to insert into a user and engage an internal surface of the user.

6. The stimulating device of claim 1, where the controller is further configured to detect pressure applied to the second outer arm and activate the vibration motor in the first outer arm in response to the detected pressure.

7. The stimulating device of claim 1, where the controller is further configured to identify a pressure pattern applied to one of the first arm and activate the vibration motor in the second outer arm with a vibration pattern that substantially mimics the pressure pattern.

8. The stimulating device of claim 1, where the central area, the at least three arms, and the controller are encompassed by an outer covering that forms a substantially waterproof barrier.

9. The stimulating device of claim 8, where the at least one pressure sensor of each of the outer arms is disposed between the outer covering and its respective outer arm.

10. The stimulating device of claim 1, where the controller is configured to operate in at least one of a vibration only mode or a feedback/response mode.

11. The stimulating device of claim 1, further comprising an input button for receiving user preferences from a user.

12. A system comprising:

a framework comprising a central area and three arms extending out from the central area in a common plane, where the three arms comprise a first outer arm, a second outer arm, and an inner arm disposed between the first outer arm and the second outer arm, where the framework includes a first set of accordion folds coupling the first outer arm to the central area and a second set of accordion folds coupling the second outer arm to the central area, and where the framework further comprises a plurality of pressure sensors and a plurality of vibration motors;

a controller coupled to the framework, the controller comprising a processing device in communication with the plurality of pressure sensors and the plurality of vibration motors, the processing device is to:

detect a pressure pattern applied to first outer arm; and activate at least one of the plurality of vibration motors disposed on the second outer arm with a vibration pattern having an intensity and duration selected in response to the detected pressure pattern; and an outer covering encasing the framework.

13. The system of claim 12, where the processor is further to receive preferences from a user.

14. The system of claim 12, where the processor is further to operate in one of a vibration-only mode or a feedback/response mode.

15. The system of claim 14, where the processor is further to receive input from a user indicative of a desire to change from one of the vibration-only mode or the feedback/response mode to a different mode.

16. The system of claim 15, where the vibration-only mode comprises a plurality of unique vibration pattern modes.

17. The system of claim 12, where the processor is further to detect a second pressure pattern applied to the second outer arm and activate a vibration motor disposed on the first outer arm with a second vibration pattern selected in response to the second pressure pattern.

18. A method comprising:

providing a framework comprising a central area and three arms extending out from the central area in a common plane, where the three arms comprise a first outer arm, a second outer arm, and an inner arm disposed between the first outer arm and the second outer arm, where the framework includes a first set of accordion folds coupling the first outer arm to the central area and a second set of accordion folds coupling the second outer arm to the central area, and where the framework further comprises a plurality of pressure sensors and a plurality of vibration motors;

providing a controller coupled to the framework, the controller comprising a processing device in communication with the plurality of pressure sensors and the plurality of vibration motors, the processing device configured to:

detect a pressure pattern applied to first outer arm; and activate at least one of the plurality of vibration motors disposed on the second outer arm with a vibration pattern having an intensity and duration selected in response to the detected pressure pattern; and providing an outer covering encasing the framework.

19. The method of claim 18, further comprising receiving preferences from a user.

20. The method of claim 18, further comprising operating in one of a vibration-only mode or a feedback/response mode.

* * * * *